(12) United States Patent
Revault et al.

(10) Patent No.: US 8,017,541 B2
(45) Date of Patent: Sep. 13, 2011

(54) CATALYST COMPONENTS BASED ON FERROCENYL COMPLEXES USED FOR OLEFIN POLYMERISATION

(75) Inventors: Cyril Revault, La Celle Saint Cloud (FR); Olivier Lavastre, Gahard (FR); Sabine Sirol, Horrues (BE)

(73) Assignees: Total Petrochemicals Research Feluy, Senefee (Feluy) (BE); Centre National de al Recherche Scientifiqaue (CNRS), Paris (FR)

( * ) Notice: Subject to any disclaimer, the term of this patent is extended or adjusted under 35 U.S.C. 154(b) by 0 days.

(21) Appl. No.: 12/295,464

(22) PCT Filed: Mar. 27, 2007

(86) PCT No.: PCT/EP2007/052909
§ 371 (c)(1),
(2), (4) Date: Oct. 4, 2010

(87) PCT Pub. No.: WO2007/113168
PCT Pub. Date: Oct. 11, 2007

(65) Prior Publication Data
US 2011/0034652 A1    Feb. 10, 2011

(30) Foreign Application Priority Data
Mar. 30, 2006    (EP) .................................... 06290539

(51) Int. Cl.
*B01J 31/22*     (2006.01)
*C08F 4/80*      (2006.01)
(52) U.S. Cl. ........ 502/113; 502/103; 502/152; 502/167; 526/113; 526/115; 526/117; 526/160; 526/161; 526/165
(58) Field of Classification Search .................. 502/103, 502/113, 152; 526/160, 161, 165, 113, 115, 526/117
See application file for complete search history.

(56) References Cited

OTHER PUBLICATIONS

Bernardi, Luca, et al., "Diastereoselective Additions of Organometallic Reagents to (SFC)-2-p-Tolylsulfanylferrocene Carboxyaldehyde and to (SFC)-2-p-tolylsulfanyl Ferrocenyl Imines. Synthesis of New Central and Planar Chiral Ferrocenyl Alcohols and Amines," Arkivoc (ii), 2004, pp. 72-90.
Bonini, Bianca F., et al., "One Pot Synthesis of New B-Lactams Containing the Ferrocene Moiety," Synlett No. 7, 2001, pp. 1092-1096.
Bosque, Ramon, et al., "Heterodi- and Heterotrimetallic Compounds Containing Five-Membered Rings and o(Pd-Csp2, ferrocene) Bonds. X-ray Crystal Structure of the Meso-Form of [Pd2(Fe(n5-C5H3)-C(CH3)=N-C6H5)}2Cl2(PPh3)2]," Organometallics, vol. 18, No. 7, 1999, pp. 1267-1274.
Bosque, Ramon, et al., "Influences of the Substituents at the Iminic Carbon Atoms (Hydrogen versus Methyl) Upon the Properties of Ferrocenylimines and their Cyclopalladated Derivatives+," Journal of Chemical Society, Dalton Transactions, 1994, pp. 735-745.
Bosque, Ramon, et al., "Substituent Effects on the Electrochemical Behavior of Iron (II) in Schiff Bases Derived from Ferrocene and their Cyclopalladated Compounds," Inorganica Chimica Acta 244, 1996, pp. 141-145.
Bullita, E., et al., "Synthesis, X-ray Structural Determination and Mossbauer Characterization of Schiff Bases Bearing Ferrocene Groups, Their Reduced Analogues and Related Complexes," Inorganica Chimica Acta 287, 1999, pp. 117-133.
Cui, Xiuling, et al., "Bis[1,1'-N,N'-(2-picolyl)aminomethyl]ferrocene as a Redox Sensor for Transition Metal Ions," Dalton Transactions, No. 11, 2004, pp. 1743-1751.
Gibson, Vernon C., et al., "Ferrocene-Substituted Bis(Imino)Pyridine Iron and Cobalt Complexes: Toward Redox-Active Catalysts for the Polymerization of Ethylene," vol. 25, No. 8, 2006, pp. 1932-1939.
Gibson, Vernon C., et al., "Synthetic, Spectroscopic and Olefin Oligomerisation Studies on Nickel and Palladium Complexes Containing Ferrocene Substituted Nitrogen Donor Ligands," Dalton Transactions, No. 5, 2003, pp. 918-926.
Lewkowski, Jaroslaw, et al., "a-(Ferrocenyl)-aminomethanephosphonous Acids. First Synthesis and Preparation of Their Esters with Cholesterol and Adenosine," Journal of Organometallic Chemistry 689, 2004, pp. 1684-1690.
Lewkowski, Jaroslaw, et al., "First Synthesis of 1,1'-ferrocene Bisaminophosphonic Esters," Journal of Organometallic Chemistry 689, 2004, pp. 1265-1270.
Lewkowski, Jaroslaw, et al., "The First Synthesis of Ferroceynl Aminophosphonic Esters," Journal of Organometallic Chemistry 631, 2001, pp. 105-109.
Lopez, Concepcion, et al., "Cyclopalladated Compounds Derived From Ferrocenylimines. Crystal Structure of [Pd{(n5-C5H5)Fe[n5-C5H3CH=N(CH2)2Ph]}Cl(PEt3)]+," Journal of Chemical Society, Dalton Transactions, Issue 1, 1992, pp. 2321-2328.
Lopez, Concepcion, et al., "Effects of the Nature of the Nitrogen Donor Atom (sp2 versus sp3) Upon the Properties and Chemistry of Palladated Complexes with a(Pd-Csp2, Ferrocene) Bonds+," Journal of Chemical Society, Dalton Transactions, 1994, pp. 3039-3046.
Lopez, Concepcion, et al., "Relationships Between 57Fe NMR, Mossbauer Parameters, Electrochemical Properties and the Structures of Ferrocenylketimines," Journal of Organometallic Chemistry 691 (2006) 475-484.
Peet, J.H.J., et al., "Novel Photoreaction Products of N-Substituted Ferroceneylimines," Journal of Organometallic Chemistry 88, 1975, pp. C1-C3.
Perez, Sonia, et al., "Trans-influences in Mononuclear Cyclopalladated Compounds Containing a a(Pd-Csp2, ferrocene) Bond. X-ray Crystal Structures of [Pd{[n5-C5H3)-Ch=N-CH2-C6H5]Fe(n5-C5H5)}(X)(PPh3)] with X-=Br- and I-," Journal of Organometallic Chemistry 625, 2001, pp. 67-76.
Revault, Cyril, et al., U.S. Appl. No. 12/295,473, filed Sep. 30, 2008, "Catalyst Components Based on Ferricinium Complexes Used for Olefin Polymerisation,".

(Continued)

*Primary Examiner* — Caixia Lu

(57) ABSTRACT

The present invention discloses catalyst components based on ferrocenyl ligands, their method of preparation and their use in the polymerization of olefins.

17 Claims, 1 Drawing Sheet

OTHER PUBLICATIONS

Walther, Dirk, "Furfurylidene-imines as Components of the Oxidative Coupling with CO2 at Nickl(0) Centers: Influence of the Subtituents on the Structure of the Resulting Nickelacycles," Zeitschrift Fuer Anorganische Und Allgemeine Chemie, vol. 628, No. 4, 2002, pp. 851-862.

Zhao, Gang, et al., "Cyclic Ether Induced Assymetric Cyclopalladation: Synthesis and Structural Characterization of Enantiopure Bis(u-acetato)-Bridged Dimers of Planar Chiral Cyclopalladated Ferrocenylimines and Their Derivatives," Organometallics No. 18, 1999, pp. 3623-3636.

CATALYST COMPONENTS BASED ON FERROCENYL COMPLEXES USED FOR OLEFIN POLYMERISATION

The present invention discloses catalyst components based on ferrocenyl ligands their method of preparation and their use in the polymerisation of olefins.

In the search for new catalyst components capable of producing highly tunable polymers, some ferrocene complexes have been known to polymerise or co-polymerise ethylene such as for example the ferrocene-substituted bis(imino) pirydine iron and cobalt complexes disclosed by Gibson et al. in Gibson V. C., Long N. J., Oxford, P. J., White A. J. P., and Williams D. J., in Organometallics ASAP article DOI: 10.1021/om0509589 or the ferrocene-substituted bis(imino) nickel and palladium complexes disclosed by Gibson et al. in J. Chem. Soc. Dalton Trans 2003, 918-926.

There is a need to develop new catalyst system having good activity and able to produce polymers tailored to specific needs.

It is an aim of the present invention to prepare new catalyst components that can be used in the polymerisation of olefins.

It is also an aim of the present invention to provide very active catalyst components.

It is another aim of the present invention to provide a method for polymerising or copolymerising olefins.

The present invention reaches, at least partially, any one of those aims.

Accordingly, the present invention discloses a catalyst system that comprises:

a) a metallic component obtained by complexation reaction of a metallic precursor $M(Hal)_n R'_{v-n}$ in a solvent, wherein M is a metal Group 6 to 10 of the Periodic Table, each Hal is the same or different and is halogen, each R' is the same or different and is substituted or unsubstituted hydrocarbyl having from 1 to 20 carbon atoms, substituted or unsubstituted aryloxy or alkoxy, v is the valence of M and n is zero or an integer at most equal to v with a ligand of formula

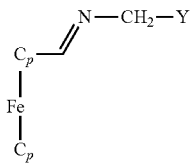

wherein Cp is a cyclopentadienyl group, unsubstituted or substituted, and wherein Y is comprises an alkyl, aryl, heterocycle or a non-heterocycle group, wherein the non-heterocycle group comprises an ether group, thioether group, phosphine group, imine group, amine group or amide group.

b) an activating agent having an ionizing action.

In a preferred embodiment according to the present invention, Y includes atoms O, N, P, S or groups —CR═CR—, —CR═N—, —N═CR— or —C≡C— wherein R is H, alkyl or aryl groups having at most 20 carbon atoms. The Y group can include a conjugation or not.

More preferably, Y is phenyl, furyl or pyridine group and $CH_2$—Y is represented by formulas

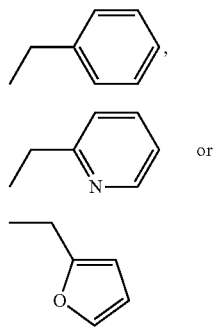

The ligands of the present invention can be prepared following the method disclosed for example in Gibson et al. ((Chem. Soc. Rev., 2004, 33, 313-328) or in Samuelson et al. (Journal of Organometallic Chemistry, 1999, 575, 108-118) or in Lewkowski et al. (Journal of Organometallic Chemistry, 2001, 631, 105-109) or in Vigota et al. (Inorganica Chimica Acta, 1999, 287, 117-133) or in Wright (Organometallics, 1990, 9, 853-856).

The ferrocenyl ligand is prepared by reacting a precursor of formula (CHO-Cp)Fe(Cp)

with an amine of formula $NH_2$—$CH_2$—Y wherein Cp and Y are as defined previously.

Figure 1:
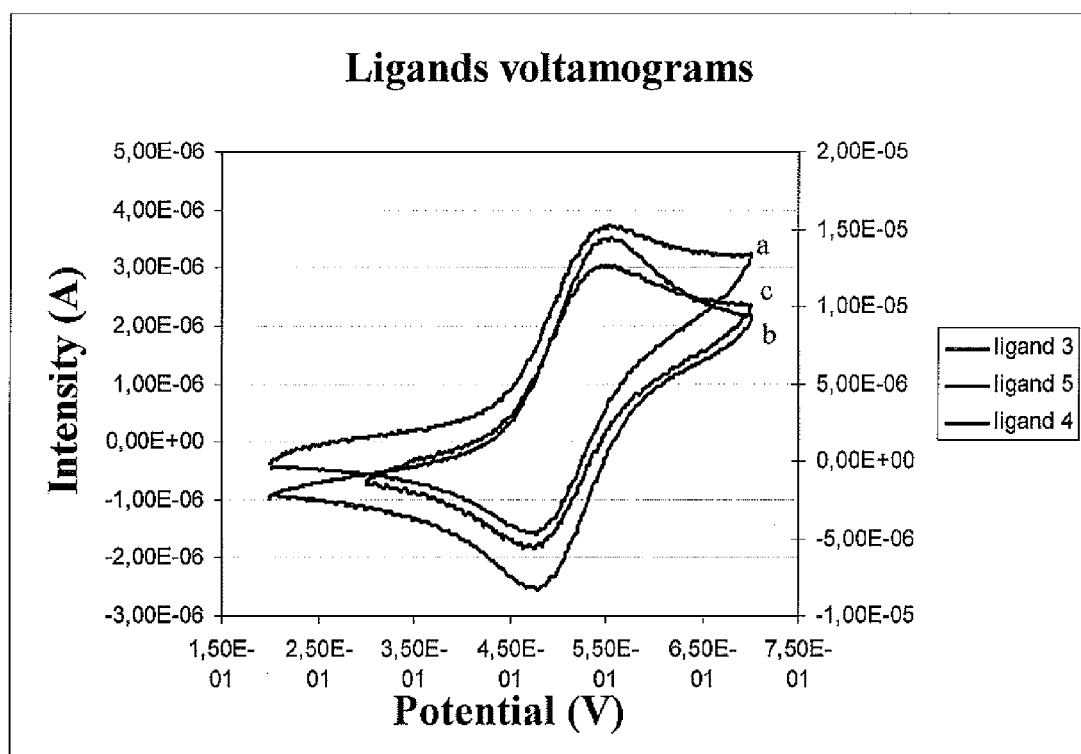
FIG. 1 represents the voltamograms of ferrocene ligand carrying different substituents Y. It is expressed as intensity in Amperes as a function of potential in Volts. Curve a represents the voltamogram of ligand 1 wherein Y is phenyl, curve b represents the voltamogram of ligand 2 wherein Y is pyridine and curve c represents the voltamogram of ligand 3 wherein Y is furyl.

The ligands of the present invention are characterised by a fully reversible status for the ferrocenylimine unit and by a total absence of conjugation between substituent group Y and metal Fe in the ligand. As the ferrocene and functional group Y are not conjugated it is allowed to modify or alter one entity, for example the ferrocene without influencing the other entity, for example the substituent Y. The electrochemical properties of the ferrocenylimines are thus fully reversible, even after modification of substituent Y. This behaviour is confirmed by electrochemical analysis of ferrocene ligands carrying different substituents Y, presented in FIG. 1. Iron has the same electronic potential for all tested substituents Y. There is thus no conjugation between the two entities.

The invention also discloses a metallic complex obtained by metalation of the ferrrocene ligand with a metal salt of formula $M(Hal)_n R'_{v-n}$ wherein M is a metal group 6 to 10 of the Periodic Table, wherein each Hal is the same or different and is halogen, wherein each R' is the same or different and is substituted or unsubstituted hydrocarbyl having from 1 to 20 carbon atoms, substituted or unsubstituted aryloxy or alkoxy, wherein v is the valence of M and n is zero or an integer at most equal to v.

Preferably M is Ni, Co, Fe, Pd or Cr.

Preferably Hal is chlorine.

Preferably n is equal to v.

The solvent may be selected from dichloromethane or tetrahydrofuran and the complexation reaction is carried out at room temperature or at reflux.

Typically, two types of metallic complexes could be formed, one where the metal is coordinated to one ligand and one where the metal is coordinated to two ligands. The relative amounts of each ligand and metal unit depend upon the nature of ligand and of the metal. The amount of ligand must therefore be of at least one equivalent of ligand per metallic equivalent.

The present invention further discloses an active catalyst system comprising the metallic complex and an activating agent having an ionising action.

Suitable activating agents are well known in the art. The activating agent can be an aluminium alkyl represented by formula $AlR^+{}_n X_{3-n}$ wherein $R^+$ is an alkyl having from 1 to 20 carbon atoms and X is a halogen. The preferred alkylating agents are triisobutyl aluminium (TIBAL) or triethyl aluminium (TEAL).

Alternatively, it can be aluminoxane and comprise oligomeric linear and/or cyclic alkyl aluminoxanes represented by formula $$R\text{----}(Al\text{---}O)_n\text{---}AlR^*{}_2$$
$$|$$
$$R^*$$

for oligomeric, linear aluminoxanes and by formula $$(\text{---}Al\text{---}O\text{---})_m$$
$$|$$
$$R^*$$

for oligomeric, cyclic aluminoxane,
wherein n is 1-40, preferably 10-20, m is 3-40, preferably 3-20 and $R^*$ is a $C_1$-$C_8$ alkyl group and preferably methyl.

The amount of activating is selected to give an Al/M ratio of from 100 to 3000, preferably of about 1000.

Suitable boron-containing activating agents may comprise a triphenylcarbenium boronate such as tetrakis-pentafluorophenyl-borato-triphenylcarbenium as described in EP-A-0427696, or those of the general formula $[L'\text{-}H]+[B\,Ar_1Ar_2X_3X_4]$— as described in EP-A-0277004 (page 6, line 30 to page 7, line 7). The amount of boron-containing activating agent is selected to give BIM ratio of from 0.5 to 5, preferably of about 1.

In another embodiment, according to the present invention, the metallic complex may be deposited on a conventional support impregnated with an activating agent. Preferably, the conventional support is silica impregnated with methylaluminoxane (MAO). Alternatively, it can be an activating support such as fluorinated alumina silica.

The present invention further discloses a method for preparing an active catalyst system that comprises the steps of:
  a) providing a ferrocenylimine ligand;
  b) complexing the ligand of step a) with a metallic salt $M(Hal)_n R'_{\nu-n}$ in a solvent;
  c) retrieving a catalyst component;
  d) activating the catalyst component with an activating agent having an ionising action;
  e) optionally adding a scavenger;
  f) retrieving an active oligomerisation or polymerisation catalyst system.

Alternatively, in step d), the catalyst component is deposited on a support impregnated with an activating agent or on an activating support.

The cocatalyst may be selected from triethylaluminium, triisobutylaluminum, tris-n-octylaluminium, tetraisobutyldialuminoxane or diethyl zinc.

The active catalyst system is used in the oligomerisation and in the polymerisation of ethylene and alpha-olefins.

The present invention discloses a methods for the oligomerisation or the polymerisation of ethylene and/or alpha-olefins that comprises the steps of:
  a) injecting the active catalyst system into the reactor;
  b) injecting the monomer and optional comonomer;
  c) maintaining under polymerisation conditions;
  d) retrieving the oligomers and/or polymer.

The polymer may be either a copolymer or a homopolymer.

The pressure in the reactor can vary from 0.5 to 50 bars, preferably from 5 to 25 bars.

The polymerisation temperature can range from 10 to 100° C., preferably from 50 to 85° C.

Preferably the monomer and optional comonomer are selected from ethylene, propylene or 1-hexene.

The present invention also discloses the polymers obtained with the new catalyst systems.

EXAMPLES

All reactions were performed using standard Schlenk techniques or in an argon-filled glove-box. The starting materials and reagents, purchased from commercial suppliers, were degassed and purified by distillation under nitrogen using standard drying agents.

Preparation of Ligands

Synthesis of N-ferrocenylidenebenzylamine (1)

All complexes were prepared according to the method described for example in Gibson et al. (Chem Soc Rev., 2004, 33, 313-328) or in Samuelson et al. (Journal of Organometallic Chemistry, 1999, 575, 108-118).

300 mg (1.4 mmol) of solid ferrocenecarboxaldehyde were introduced in a schlenk. 90 μL (2.1 mmol) of benzylamine and 2 mg of p-toluene sulfonic acid were added. The mixture was dissolved in 20 mL of toluene and the homogeneous mixture was stirred and heated at reflux overnight (16 h). The solution was cooled down to room temperature (25° C.) and the solvent was vaporised under vacuum. After drying overnight under vacuum and at a temperature of 50° C., 374.7 mg (1.28 mmol) of orange solid were obtained with a yield of 91%.

$RMN^1H$ (200 MHz, $CDCl_3$): δ 8.26 (s, CH=N, 1H); 7.4-7.3 (m, ArH, 5H); 4.73 (m, $C_5H_4$, 2H); 4.69 (s, $CH_2Ph$, 2H); 4.31 (m, $C_5H_4$, 2H); 4.20 (s, $C_5H_5$, 5H)

Synthesis of N-ferrocenylidenepyridinylmethanamine (2)

300 mg (1.4 mmol) of solid ferrocenecarboxaldehyde were introduced in a schlenk. 138 μL (2.1 mmol) of aminomethylpyridine were added. The mixture was dissolved in 20 mL of toluene and the homogeneous mixture was stirred and heated at reflux overnight (16 h). The solution was cooled down to room temperature and the solvent was vaporised under vacuum. After drying overnight under vacuum and at a temperature of 50° C., 379 mg (1.25 mmol) of orange solid were obtained with a yield of 89%.

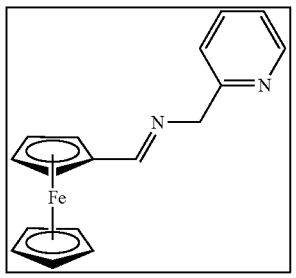

RMN$^1$H (200 MHz, CDCl$_3$): δ 8.58 (m, H$_{pyr}$, 1H); 8.34 (s, CH=N, 1H); 7.68 (m, H$_{pyr}$, 1H); 7.38 (m, H$_{pyr}$, 1H); 7.17 (m, H$_{pyr}$, 1H), 4.80 (s, CH$_2$, 2H); 4.70 (m, C$_5$H$_4$, 2H); 4.40 (m, C$_5$H$_4$, 2H); 4.18 (s, C$_5$H$_5$, 5H).

Synthesis of N-ferrocenylidenefurfurylamine (3)

300 mg (1.4 mmol) of solid ferrocenecarboxaldehyde were introduced in a schlenk. 138 μL (2.1 mmol) of furylamine and 2 mg of p-toluene sulfonic acid were added. The mixture was dissolved in 20 mL of toluene and the homogeneous mixture was stirred and heated at reflux overnight (16 h). The solution was cooled down to room temperature and the solvent was vaporised under vacuum. After drying overnight under vacuum and at a temperature of 50° C., 381 mg (1.30 mmol) of orange solid were obtained with a yield of 93%.

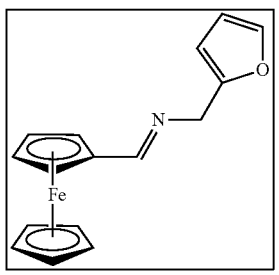

RMN$^1$H (200 MHz, CDCl$_3$): δ 8.20 (s, CH=N, 1H); 7.39 (m, H$_{fur}$, 1H); 6.35 (m, H$_{fur}$, 1H); 6.26 (m, H$_{fur}$, 1H); 4.68 (m, C$_5$H$_4$, 2H); 4.61 (s, CH$_2$, 2H), 4.39 (m, C$_5$H$_4$, 2H); 4.18 (s, C$_5$H$_5$, 5H).

Complexation of Ferrocenyl Ligands with Metallic Precursors

Complexation of Ligand N-Ferrocenylidenebenzylamine (1)

With CrCl$_2$.

2.46 mg (20 μmol) of metallic precursor CrCl$_2$ were introduced in a schlenk. 11.7 mg (40 μmol) of ligand 1 were added. The solids were dissolved in 200 μL of tetrahydrofuran (THF) to reach a concentration of 0.1 mol/L. The solution was stirred at room temperature for a period of time of 3 h and the solvent was vaporised. A dark solid was obtained.

With CrCl$_3$.

7.49 mg (20 μmol) of metallic precursor CrCl$_3$.3THF were introduced in a schlenk. 11.7 mg (40 μmol) of ligand 1 were added. The solids were dissolved in 200 μL of tetrahydrofuran (THF) to reach a concentration of 0.1 mol/L. The solution was stirred at room temperature for a period of time of 3 h and the solvent was vaporised. A dark solid was obtained.

Complexation of Ligand N-Ferrocenylidenepyridinylmethanamine (2)

With CrCl$_7$.

2.46 mg (20 μmol) of metallic precursor CrCl$_2$ were introduced in a schlenk. 11.7 mg (40 μmol) of ligand 2 were added. The solids were dissolved in 200 μL of tetrahydrofuran (THF) to reach a concentration of 0.1 mol/L. The solution was stirred at room temperature for a period of time of 3 h and the solvent was vaporised. A dark solid was obtained.

With CrCl$_3$.

7.49 mg (20 μmol) of metallic precursor CrCl$_3$.3THF were introduced in a schlenk. 11.7 mg (40 μmol) of ligand 2 were added. The solids were dissolved in 200 μL of tetrahydrofuran (THF) to reach a concentration of 0.1 mol/L. The solution was stirred at room temperature for a period of time of 3 h and the solvent was vaporised. A dark solid was obtained.

Complexation of ligand N-ferrocenylidenefurfurylamine (3)

With CrCl$_2$.

2.46 mg (20 μmol) of metallic precursor CrCl$_2$ were introduced in a schlenk. 12.2 mg (40 μmol) of ligand 3 were added. The solids were dissolved in 200 μL of tetrahydrofuran (THF) to reach a concentration of 0.1 mol/L. The solution was stirred at room temperature for a period of time of 3 h and the solvent was vaporised. A dark solid was obtained.

With CrCl$_3$.

7.49 mg (20 μmol) of metallic precursor CrCl$_3$.3THF were introduced in a schlenk. 12.2 mg (40 μmol) of ligand 3 were added. The solids were dissolved in 200 μL of tetrahydrofuran (THF) to reach a concentration of 0.1 mol/L. The solution was stirred at room temperature for a period of time of 3 h and the solvent was vaporised. A dark solid was obtained.

Polymerisation of Ethylene.

The metallic complexes obtained in the previous step were activated with 100 equivalents with respect to metal Cr of methylaluminoxane (MAO) 30% in toluene.

The addition of total MAO was carried out in two steps:
1. as activator; and
2. as scavenger, mixed with toluene.

The catalyst component was deposited in a schlenk and 325 μL of MAO (30%) were added to the schlenk as activating agent. The solution was stirred for 5 minutes and then diluted with 4.7 mL of toluene.

The reactor was dried under nitrogen at a temperature of 110° C. for a period of time of 30 minutes. The temperature was raised to 35° C. and 50 mL of toluene were added to the reactor under nitrogen reflux. A solution of scavenger consisting of 100 μl of MAO at 30% and 4.9 mL of toluene were added to the reactor and the solution was stirred during a few minutes. 20 μmol of the selected catalyst component were added to the reactor under nitrogen reflux. The nitrogen flux was stopped, the reactor was purged and placed under an ethylene pressure of 15 bars. Stirring was continued for a period of time of one hour. The reactor was then purged and the polymerisation was stopped by addition of a 10% solution of MeOH/HCl. The polymer was washed three times with 30 mL of methanol and 30 mL of acetone and dried under vacuum overnight at room temperature. The results are presented in Table I.

TABLE I

| Metal salt | Ligand | MAO Eq. | Activity Kg(PE)/mol(cata)/h | DSC Tm° C. |
|---|---|---|---|---|
| $CrCl_2$ | 1 | 100 | 13.1 | 137 |
| $CrCl_2$ | 3 | 100 | 14.3 | 134 |
| $CrCl_3$ | 3 | 100 | 8.21 | 132 |

The invention claimed is:

1. A method for preparing a catalyst system that comprises the steps of:
    a) providing a metallic precursor $M(Hal)_n R'_{v-n}$ in a solvent, wherein M is a metal Group 6 to 10 of the Periodic Table, each Hal is the same or different and is halogen, each R' is the same or different and is substituted or unsubstituted hydrocarbyl having from 1 to 20 carbon atoms, substituted or unsubstituted aryloxy or alkoxy, v is the valence of M and n is zero or an integer at most equal to v;
    b) complexing the metallic precursor of step a) with a ligand of formula

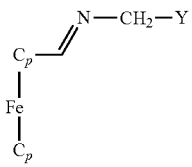

wherein Cp is a cyclopentadienyl group, unsubstituted or substituted, and
    wherein Y comprises an alkyl, aryl, heterocycle or a non-heterocycle group,
    wherein the non-heterocycle group comprises an ether group, thioether group, phosphine group, imine group, amine group or amide group
    c) adding an activating agent having an ionizing action.

2. The method of claim 1 wherein Y includes atoms O, N, P, or S, or groups —CR=CR—, —CR=N—, —N=CR— or —C≡C— wherein R is H, alkyl or aryl groups having at most 20 carbon atoms and wherein the Y group optionally includes a conjugation.

3. The method of claim 1 wherein group $CH_2$—Y is selected from

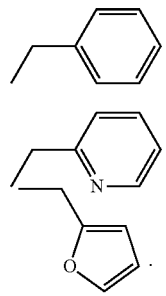

4. The method of claim 1 wherein M is Ni, Co, Cr, Pd or Fe.
5. The method of claim 4 wherein M is Cr.
6. The method of claim 1 wherein Hal is chlorine and wherein (v-n) is 0.

7. An active catalyst system obtained by the method of claim 1.
8. A method for polymerizing ethylene and/or alpha-olefins that comprises the steps of:
    a) injecting the active catalyst system of claim 7 into the reactor;
    b) injecting the monomer and optional comonomer;
    c) maintaining under polymerization conditions;
    d) retrieving the polymer.
9. The method of claim 8 wherein the polymer is a copolymer.
10. The method of claim 9 wherein the monomer and comonomer are selected from ethylene, propylene or hexene.
11. The method of claim 8 wherein the polymer is a homopolymer.
12. A method for oligomerizing ethylene and/or alpha-olefins that comprises the steps of:
    a) injecting the active catalyst system of claim 7 into the reactor;
    b) injecting the monomer and optional comonomer;
    c) maintaining under polymerization conditions;
    d) retrieving the oligomers.
13. A ligand of formula:

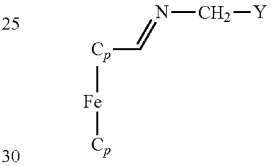

wherein Cp is a cyclopentadienyl group, unsubstituted or substituted, and
    wherein Y comprises an alkyl, aryl, heterocycle or a non-heterocycle group,
    wherein the non-heterocycle group comprises an ether group, thioether group, phosphine group, imine group, amine group or amide group.
14. The ligand of claim 13 wherein Y includes atoms O, N, P, or S, or groups —CR=CR—, —CRN—, —N=CR— or wherein R is H, alkyl or aryl groups having at most 20 carbon atoms and wherein the Y group optionally includes a conjugation.
15. The ligand of claim 13 wherein group $CH_2$—Y is selected from:

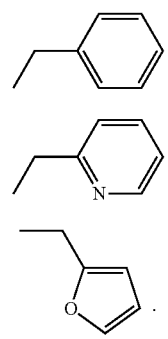

16. The ligand of claim 13 M is Ni, Co, Cr, Pd or Fe.
17. The ligand of claim 13 wherein Hal is chlorine and wherein (v-n) is 0.

* * * * *

UNITED STATES PATENT AND TRADEMARK OFFICE
CERTIFICATE OF CORRECTION

PATENT NO. : 8,017,541 B2  
APPLICATION NO. : 12/295464  
DATED : September 13, 2011  
INVENTOR(S) : Cyril Revault et al.

Page 1 of 1

It is certified that error appears in the above-identified patent and that said Letters Patent is hereby corrected as shown below:

Title page, item "(73) Assignees: Total Petrochemicals Research Feluy, Senefee (Feluy) (BE); Centre National de al Recherche Scientifiqaue (CNRS), Paris (FR)"

should read:

--(73) Assignees: Total Petrochemicals Research Feluy, Seneffe (Feluy) (BE); Centre National de la Recherche Scientifique (CNRS), Paris (FR)--

Signed and Sealed this  
First Day of November, 2011

David J. Kappos  
*Director of the United States Patent and Trademark Office*